(12) United States Patent
Croll

(10) Patent No.: US 6,986,924 B2
(45) Date of Patent: Jan. 17, 2006

(54) DISPOSABLE ADHESIVE DELIVERY PAD FOR DENTAL CLEANING PASTES AND SOLUTIONS

(76) Inventor: Theodore P. Croll, 4242 Mechanicsville Rd., Mechanicsville, PA (US) 18934

( * ) Notice: Subject to any disclaimer, the term of this patent is extended or adjusted under 35 U.S.C. 154(b) by 205 days.

(21) Appl. No.: 10/735,781

(22) Filed: Dec. 16, 2003

(65) Prior Publication Data

US 2005/0129893 A1  Jun. 16, 2005

(51) Int. Cl.
*A61C 3/00* (2006.01)
(52) U.S. Cl. .................. 428/40.1; 428/40.9; 428/42.1; 428/121; 433/163
(58) Field of Classification Search ............. 428/40.1, 428/40.9, 42.1, 121; 433/163
See application file for complete search history.

(56) References Cited

U.S. PATENT DOCUMENTS

| 4,988,296 A * | 1/1991 | Spencer ........................ 433/163 |
| 6,257,888 B1 * | 7/2001 | Barham ....................... 433/163 |

* cited by examiner

*Primary Examiner*—Nasser Ahmad
(74) *Attorney, Agent, or Firm*—Gregory J. Gore

(57) ABSTRACT

A foil sheet of semi-rigid laminated material provides a disposable adhesive pad which includes adhesive on portions of opposing top and bottom surfaces. On a portion of the top side an adhesive is covered by a peel-off label that preferably includes advertising. The remainder of the top surface is substantially a fictionless foil surface. The opposite bottom side is also provided with an adhesive on a portion of its surface. The foil is a medical metal foil that is insoluble in saliva, prophylactic paste, and water. The device is substantially planar, however two wings may be formed along foldlines which provide sidewalls that extend upwardly from the top surface and contain a dental material such as a cleaning paste, holding it on the foil portion of the pad.

6 Claims, 3 Drawing Sheets

DISPOSABLE ADHESIVE DELIVERY PAD FOR DENTAL CLEANING PASTES AND SOLUTIONS

FIELD OF THE INVENTION

The present invention relates to devices for hand-holding tooth preparation compounds in dentistry. More specifically, it relates to a paste or solution holding device which is adhesively attached to the dentist's or hygienist's glove.

BACKGROUND OF THE INVENTION

In dentistry, a dental cleaning is called a prophylaxis and the cleaning paste is called prophylaxis paste. Such paste is most commonly provided in two ways: either in bulk in a large container from which one scoops out a portion with a spatula, or in individual dose cups. The paste is usually placed into a plastic or metal cup retainer attached to the dentist's or hygienist's gloved finger as it is being used. The individual dose cups are sometimes attached to the glove by an adhesive dot with adhesive material on both sides to retain the cup to the glove. The problem with some of these systems of holding the working compound is that the plastic or metal cup holders traditionally used require cleaning and sterilization.

SUMMARY OF THE INVENTION

In order to solve the problems in the art described above, the present disposable adhesive pad has been devised. The invention comprises a foil sheet of semi-rigid laminated material which includes adhesive on portions of opposing top and bottom surfaces. On a portion of the top side an adhesive is covered by a peel-off label that preferably includes advertising. The remainder of the top surface is a substantially frictionless foil surface. The opposite bottom side is also provided with an adhesive on a portion of its surface. The foil is a medical metal foil that is insoluble in saliva, prophylactic paste, and water.

The device is substantially planar, however two wings may be formed along foldlines which provide sidewalls that extend upwardly from the top surface and contain the paste, holding it on the foil portion of the pad. If the adjacent walled portion is used to contain the paste, it may be picked up by the rotating rubber cleaning cup as needed during the dental cleaning. When the top side label is peeled off, the adhesive underneath is available for placement of the dose cup type of prophylactic paste packaging. Once the cleaning is completed, the rubber glove is removed and the prophy pad discarded along with any residual paste. The present invention provides a totally disposable device that saves time and trouble of cleaning and sterilization required by the traditional plastic or metal cup holders. Other objects and advantages of the present invention will be readily apparent to those of skill in the art from the following drawings and description of the preferred embodiments.

DESCRIPTION OF THE PREFERRED EMBODIMENT

Figure 1:
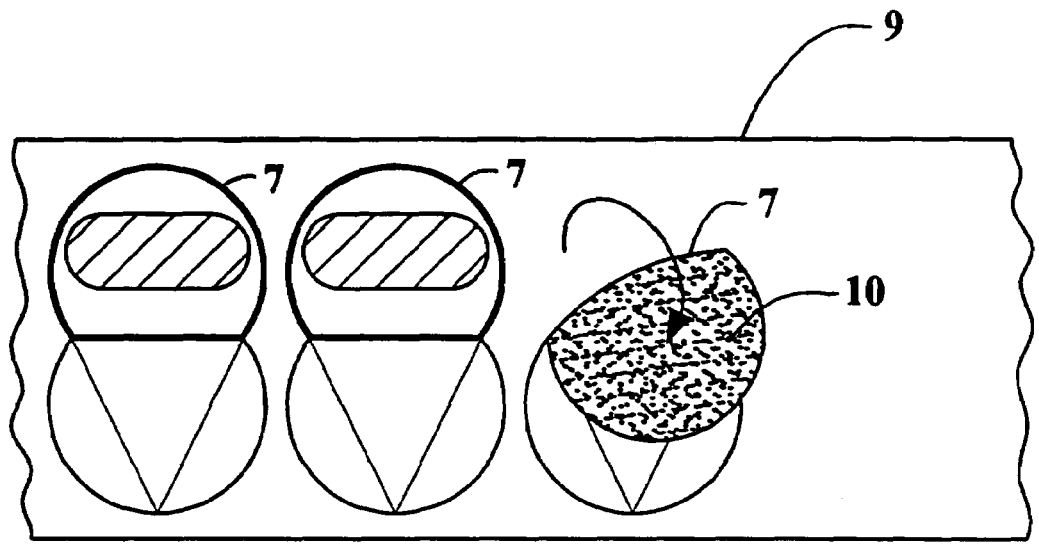
FIG. 1 is a front elevation view of a series of disposable pads positioned on a carrier strip. One pad is partially peeled back to expose the adhesive on the bottom side.
Figure 4:
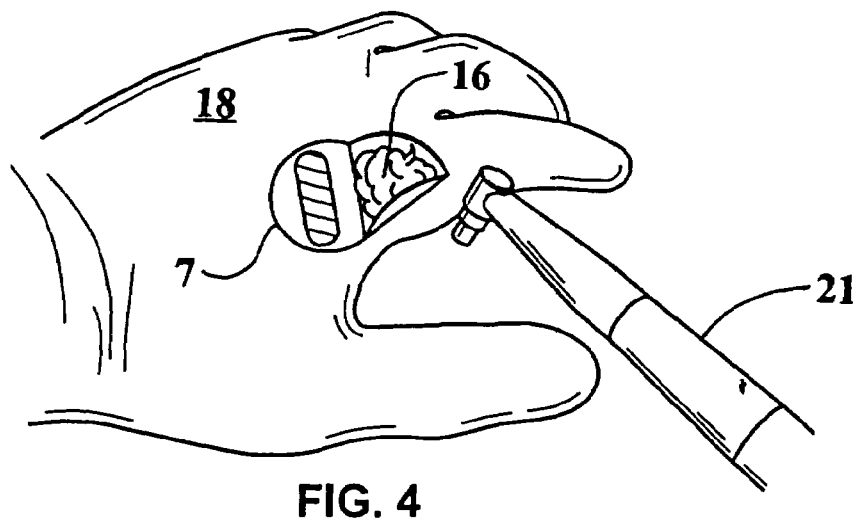
FIG. 4 is a top left rear perspective view of the present invention placed on a gloved hand while in use.

Referring now to FIG. 1, the present invention is shown in its bulk manufactured state comprising a plurality of delivery pads 7 adhesively held on the manufacturing carrier strip 9. Because the invention is comprised of several adhesively laminated paper components, it may be produced inexpensively by label manufacturing equipment. Each individual delivery pad may be peeled off the carrier strip as it is needed just before use. The pad farthest to the right in FIG. 1 reveals an adhesive 10 on the bottom side of the pad, which after removal from the carrier strip, is immediately pressed against the hand or clinician's glove to hold the pad in place as shown in FIG. 4 below. The bottom side adhesive material does not cover the undersides of the fold-up wings 14 but covers the rest of the underside to provide firm attachment to the glove.

Figures 2, 3:
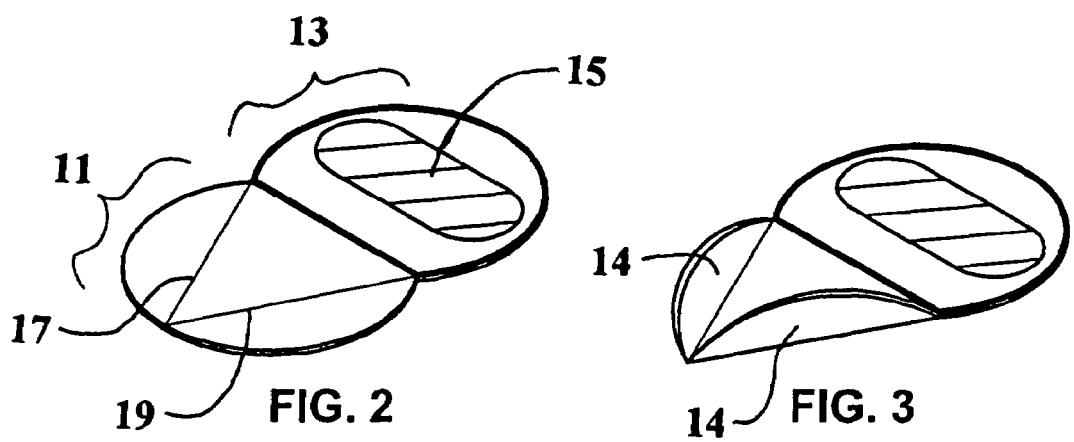
FIG. 2 is a top right front perspective view of a delivery pad of the invention.
FIG. 3 is a top right front perspective view with angled sidewalls folded upwardly.

Referring now to FIG. 2, the delivery pad of the invention includes two main portions, a containment or delivery portion 11 and an attachment portion 13. The attachment portion includes a top side adhesive covered by a releasable paper label that preferably includes advertising 15. Scored foldlines 17 and 19 on the delivery portion allow sides of the delivery pad to fold upwardly to provide containment sidewalls 14 for a dental paste or other working material as shown in FIG. 3.

Referring now to FIG. 4, the delivery pad 7 is shown attached to the glove 18 of the clinician with the sidewall wings folded upwardly to create a containment pocket on the delivery portion so that the paste 16 may be scooped in the usual fashion with the rubber cleaning cup of the clinician's handpiece 21. A metal foil provides an ideal surface of reduced friction to adequately hold the paste yet permits its easy removal. The foil material is preferably of the type such as 7 pt. 5 silver foil laminated board produced by the Fasson Roll North America, a division of Avery Dennison.

Figure 5:
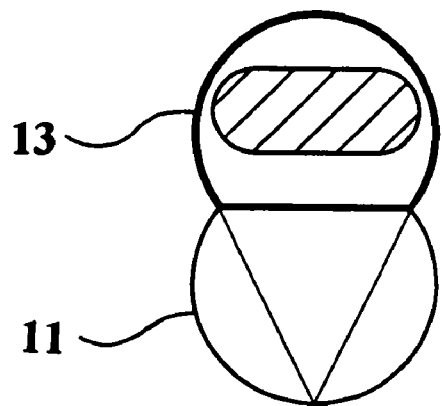
FIG. 5 is a front view of the invention.
Figure 6:
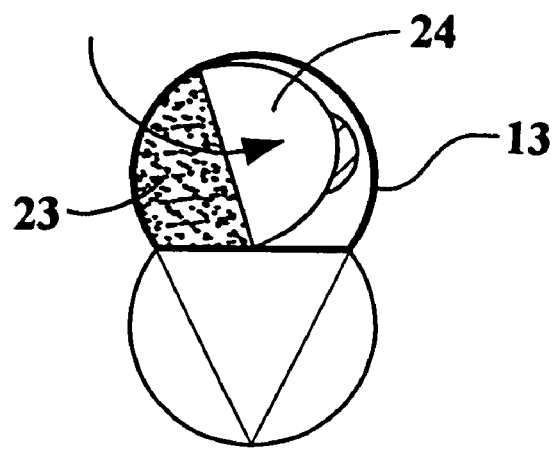
FIG. 6 is a front view of the invention with the label partially peeled from the top side of the delivery pad.
Figure 7:
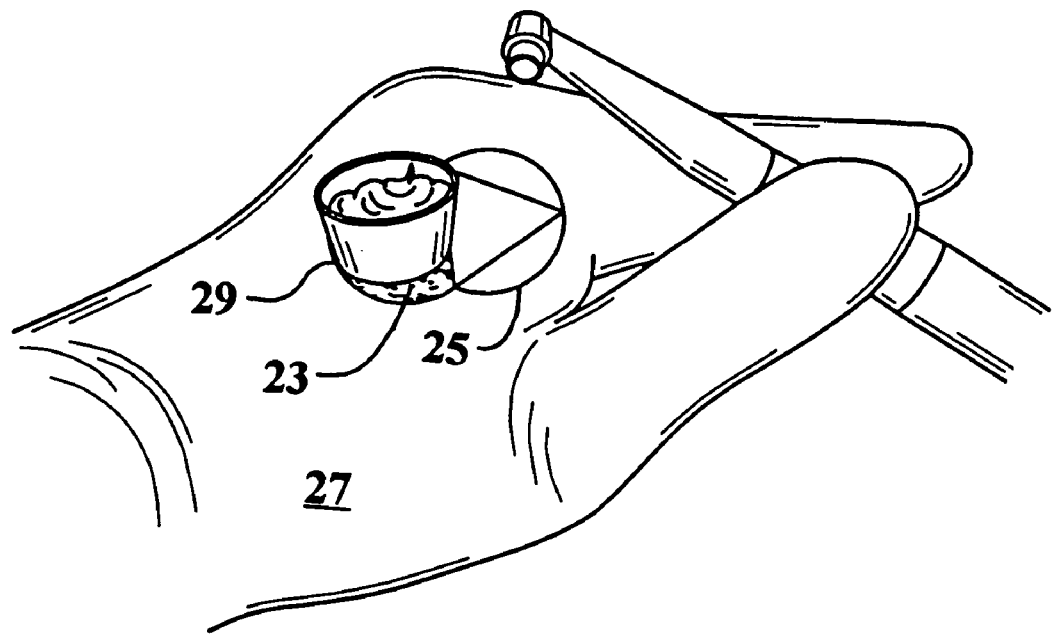
FIG. 7 is a top front isometric view of the invention alternately used to adhesively hold a prophylactic dose cup on the glove of the dental clinician or hygienist.

Referring now to FIGS. 5, 6, and 7, the present invention is shown in a different application. As shown in FIG. 5, the invention is identical having a delivery portion 11 and attachment portion 13 except that as illustrated in FIG. 6, the top paper cover 24 of the attachment portion 13 of the label is removed to reveal an adhesive layer 23 underneath. The result is a foil substrate with adhesive on both sides. When in use as shown in FIG. 7, one side holds the foil board 25 to the glove 27 while the top side may be used to hold a dose cup 29 for prophylactic paste or other dental material thus securing the cup to the glove. In this application, the delivery pad is not used but it provides a second utility for the invention if the clinician desires to use a dose cup.

Figure 8:
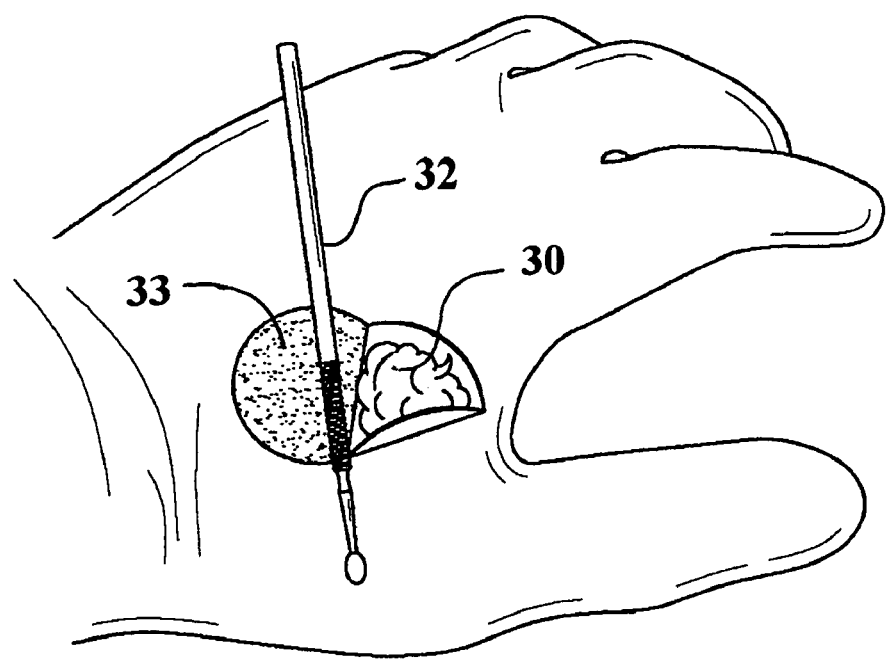
FIG. 8 is a top front isometric view of the invention alternately used to hold a dental material and adhesively secure a small dental instrument.
Figure 9:
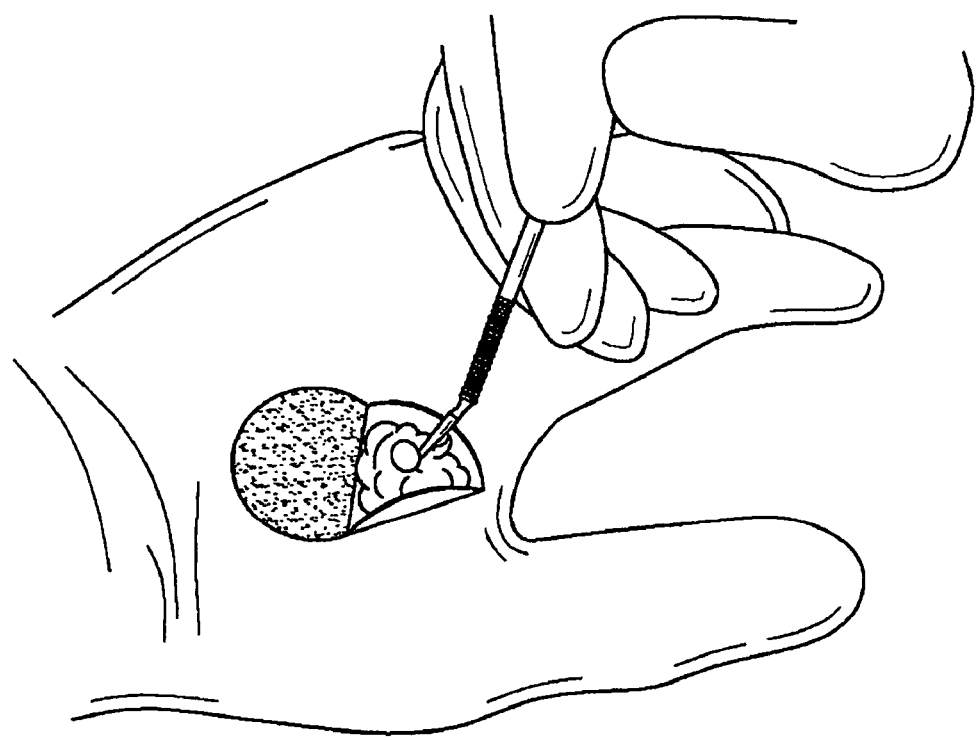
FIG. 9 is a top front isometric view showing the dental instrument released from the adhesive holding portion of the delivery pad and being manually applied to the contained dental material.

The present device may serve other uses and may provide a disposable adhesive delivery pad for application of other dental materials. For example, as shown in FIGS. 8 and 9, the dentist or hygienist is applying a bonded resin seal into a tooth. A portion of the liquid resin 30 could be carried on the non-adhesive section of the delivery pad for pick-up by a microbrush applicator 32. The adhesive section of the top of the pad 33 can be exposed and serve as an attachment mechanism to secure the applicator 32 at times when the clinician does not need to use it. This is exceptionally helpful when a procedure is being performed by a sole operator, who has no assistant from whom to receive materials or instruments. Another practical example which would provide such a convenience would be when an orthodontic assistant who has the chore of bonding many orthodontic brackets to teeth using light-cured resin material. The delivery pad of the invention therefore serves as not only a holder for dental pastes and solutions but also as a temporary holder for small dental instruments.

From the foregoing, it will be readily understood by those of skill in the art that the present invention provides both a disposable dental paste delivery system for bulk dental pastes or other dental materials and also a convenient means of attachment of material packaged in the form of a dose cup. The non-adhesive portion of the pad may also be used to serve as a delivery point for various types of dental materials such as dental cements, resin restorative materials, or even medicaments that need to be applied to structures in the mouth. The adhesive section of the top surface of the pad may be used to temporarily secure a small arrnlicator brush or instrument or provide a surface for attachment of any small item that the dentist or hygienist may need to complete a dental procedure. Because it can be inexpensively produced by label-printing manufacturing methods, the addition of printed advertising on the top cover of the attachment portion may be inexpensively included as an additional benefit. Also, although the preferred embodiment shows the use of two upwardly folded angled sidewalls, it will be understood that a greater number of sidewalls formed along additional foidlines may similarly be employed to contain the working material. It should be understood that there may be other modifications and changes to the present invention that will be obvious to those of skill in the art from the foregoing description, however, the present invention should be limited only by the following claims and their legal equivalents.

What is claimed is:

1. A dental material delivery pad for adhesive attachment to a hand or glove, comprising:
   a planar delivery pad comprising a paper board laminated with metal foil, said pad having a delivery portion and an attachment portion, a top surface and a bottom surface; an adhesesive on the bottom surface of the attachment portion of said pad; and
   a plurality of foldlines on the top surface of the delivery portion of said pad for forming sidewall portions of said pad, said sidewalls being upwardly foldable along said foldlines for facilitating the containment of dental material on said delivery portion of said pad.

2. The delivery pad of claim 1 further including an adhesive on the top surface of the attachment portion of said pad.

3. The delivery pad of claim 2 further including a peel-off label covering the adhesive on the top portion of said pad.

4. The delivery pad of claim 3 wherein said peel-off label further includes printed advertising.

5. The delivery pad of claim 1 wherein said foldlines are convergent to a point on the edge of the pad in the direction extending away from said attachment portion.

6. An arrangement of dental material delivery pads comprising a plurality of delivery pads as described in claim 1, said pads being arranged in a row and each individually adhesively affixed to a carrier strip.

* * * * *